United States Patent
Drew

(10) Patent No.: US 9,743,878 B2
(45) Date of Patent: Aug. 29, 2017

(54) EVENT-BASED LEAD IMPEDANCE MONITORING

(75) Inventor: Touby A. Drew, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1861 days.

(21) Appl. No.: 11/413,072

(22) Filed: Apr. 27, 2006

(65) Prior Publication Data

US 2006/0264777 A1    Nov. 23, 2006

Related U.S. Application Data

(60) Provisional application No. 60/676,250, filed on Apr. 29, 2005.

(51) Int. Cl.
*A61N 1/00* (2006.01)
*A61B 5/00* (2006.01)
(Continued)

(52) U.S. Cl.
CPC ............ *A61B 5/4094* (2013.01); *A61B 5/048* (2013.01); *A61B 5/053* (2013.01); *A61N 1/36082* (2013.01); *A61N 1/0529* (2013.01)

(58) Field of Classification Search
CPC ....... A61B 5/053; A61B 5/4094; A61B 5/048; A61N 1/0529; A61N 1/36082
(Continued)

(56) References Cited

U.S. PATENT DOCUMENTS

| | | | | |
|---|---|---|---|---|
| 4,279,258 A | * | 7/1981 | John | 600/544 |
| 4,630,615 A | * | 12/1986 | Yomtov | 600/547 |

(Continued)

FOREIGN PATENT DOCUMENTS

| | | |
|---|---|---|
| EP | 0 715 866 A2 | 6/1996 |
| EP | 1 462 146 A1 | 9/2004 |

(Continued)

OTHER PUBLICATIONS

Notification of Transmittal of the International Search Report and the Written Opinion dated Nov. 16, 2006, for corresponding International Application No. PCT/US2006/016434, 12 pages.
(Continued)

*Primary Examiner* — Lindsey G Wehrheim
(74) *Attorney, Agent, or Firm* — Shumaker & Sieffert, P.A.

(57) ABSTRACT

A medical device senses electrical activity within a patient and, in some embodiments, delivers stimulation to the patient via a plurality electrical paths, which include electrodes and associated conductors of one or more leads. The medical device determines whether a symptomatic event, such as a seizure, is detected based on the sensed electrical activity, and measures the impedance of one or more of the paths in response to the determination. If the medical device identifies a dysfunctional electrical path based on the measured impedance, the device may, as examples, disable the dysfunctional electrical path, or modify a stimulation or sensing program to not use the dysfunctional electrical path. In this manner, the medical device may identify inaccurate symptomatic event detection and, where the device delivers a therapy in response to such detection, such as stimulation via the electrical paths, avoid inappropriate therapy delivery.

34 Claims, 4 Drawing Sheets

(51) Int. Cl.
*A61B 5/048* (2006.01)
*A61B 5/053* (2006.01)
*A61N 1/36* (2006.01)
*A61N 1/05* (2006.01)

(58) Field of Classification Search
USPC .......... 607/45–46, 55–57, 117–118; 600/544
See application file for complete search history.

(56) References Cited

U.S. PATENT DOCUMENTS

| | | | |
|---|---|---|---|
| 4,722,342 A | | 2/1988 | Amundson |
| 4,899,750 A | * | 2/1990 | Ekwall ............................ 607/28 |
| 5,003,975 A | * | 4/1991 | Hafelfinger et al. ........... 607/28 |
| 5,381,804 A | * | 1/1995 | Shambroom ................. 600/544 |
| 5,507,786 A | | 4/1996 | Morgan et al. |
| 5,534,018 A | | 7/1996 | Wahlstrand et al. |
| 5,593,431 A | | 1/1997 | Sheldon |
| 5,741,311 A | | 4/1998 | Mc Venes et al. |
| 5,755,742 A | | 5/1998 | Schuelke et al. |
| 5,891,179 A | * | 4/1999 | Er et al. ........................ 607/27 |
| 5,957,861 A | | 9/1999 | Combs et al. |
| 5,957,957 A | | 9/1999 | Sheldon |
| 6,188,927 B1 | | 2/2001 | Lu et al. |
| 6,317,633 B1 | | 11/2001 | Jorgenson et al. |
| 6,360,123 B1 | | 3/2002 | Kimchi et al. |
| 6,490,486 B1 | | 12/2002 | Bradley |
| 6,516,227 B1 | | 2/2003 | Meadows et al. |
| 6,549,804 B1 | | 4/2003 | Osorio et al. |
| 6,658,287 B1 | * | 12/2003 | Litt ...................... A61B 5/0476 |
| | | | 600/544 |
| 6,721,600 B2 | * | 4/2004 | Jorgenson et al. ............. 607/27 |
| 6,760,624 B2 | | 7/2004 | Anderson et al. |
| 6,978,171 B2 | * | 12/2005 | Goetz et al. ................. 600/547 |
| 7,164,944 B1 | * | 1/2007 | Kroll et al. ........................ 607/2 |
| 7,493,159 B2 | | 2/2009 | Hrdlicka et al. |
| 7,536,227 B1 | * | 5/2009 | Poore et al. ................. 607/118 |
| 7,574,259 B1 | * | 8/2009 | Pei ......................... A61N 1/056 |
| | | | 607/28 |
| 8,355,783 B2 | | 1/2013 | Goetz et al. |
| 2002/0002389 A1 | | 1/2002 | Bradley et al. |
| 2002/0120307 A1 | | 8/2002 | Jorgenson et al. |
| 2002/0147473 A1 | | 10/2002 | Seim et al. |
| 2002/0177881 A1 | | 11/2002 | Conley et al. |
| 2003/0036772 A1 | | 2/2003 | Saphon et al. |
| 2003/0125778 A1 | | 7/2003 | Cho et al. |
| 2003/0176807 A1 | * | 9/2003 | Goetz et al. ................. 600/547 |
| 2004/0064161 A1 | | 4/2004 | Gunderson et al. |
| 2004/0138711 A1 | | 7/2004 | Osorio et al. |
| 2004/0162593 A1 | | 8/2004 | Jorgenson et al. |
| 2005/0065554 A1 | | 3/2005 | Kenknight et al. |
| 2005/0080460 A1 | | 4/2005 | Wang et al. |
| 2005/0090870 A1 | | 4/2005 | Hine et al. |
| 2005/0096704 A1 | | 5/2005 | Freeberg |
| 2005/0222522 A1 | | 10/2005 | Heruth et al. |
| 2005/0244377 A1 | * | 11/2005 | Sigg ................... C12N 15/1138 |
| | | | 424/93.2 |
| 2006/0015148 A1 | | 1/2006 | McCabe et al. |
| 2006/0025828 A1 | * | 2/2006 | Armstrong et al. ............ 607/28 |
| 2006/0241711 A1 | * | 10/2006 | Sathaye ............. A61N 1/36521 |
| | | | 607/28 |
| 2006/0265024 A1 | | 11/2006 | Goetz et al. |
| 2006/0265025 A1 | | 11/2006 | Goetz et al. |
| 2008/0058892 A1 | * | 3/2008 | Haefner et al. ................ 607/45 |

FOREIGN PATENT DOCUMENTS

| | | | | |
|---|---|---|---|---|
| NZ | WO 2005018448 A1 | * | 3/2005 | ........... A61B 5/0476 |
| WO | WO 03/077992 A1 | | 9/2003 | |
| WO | WO 2004/034883 A2 | | 4/2004 | |
| WO | WO 2006/041738 A2 | | 4/2006 | |

OTHER PUBLICATIONS

Notification of Transmittal of the International Preliminary Report on Patentability dated Mar. 30, 2007, for corresponding International Application No. PCT/US2006/016434, filed Apr. 27, 2006 (8 pgs.).
Office Action dated May 26, 2010 for U.S. Appl. No. 11/414,786 (7 pgs.).
Advisory Action dated Aug. 10, 2010 for U.S. Appl. No. 11/414,786 (3 pgs.).
Request for Continued Examination and Amendment dated Sep. 27, 2010 for U.S. Appl. No. 11/414,786 (11 pgs.).
Responsive Amendment dated Aug. 29, 2012 for U.S. Appl. No. 12/577,071, (12 pgs.).
Office Action from U.S. Appl. No. 11/414,786, dated Aug. 15, 2012, 11 pp.
Response to Office Action dated Aug. 15, 2012, from U.S. Appl. No. 11/414,786, filed Oct. 15, 2012, 12 pp.
Office Action from U.S. Appl. No. 11/414,786, dated Oct. 27, 2014, 10 pp.
Office Action from U.S. Appl. No. 11/414,789, dated May 21, 2015, 7 pp.
Office Action dated Jun. 5, 2012 for U.S. Appl. No. 12/577,071, (9 pgs.).
Office Action dated Oct. 13, 2011 for U.S. Appl. No. 11/414,786, (9 pgs.).
Responsive Amendment dated Jan. 13, 2012 for U.S. Appl. No. 11/414,786, (17 pgs.).
Response to Office Action dated Oct. 27, 2014, U.S. Appl. No. 11/414,786, filed Jan. 22, 2015, 13 pp.
Examiner's Answer from U.S. Appl. No. 11/414,786, dated Jun. 3, 2016, 10 pp.
Office Action dated Dec. 30, 2009 for U.S. Appl. No. 11/414,786 (8 pgs.).
Response dated Mar. 1, 2010 for U.S. Appl. No. 11/414,786 (9 pgs.).
Prosecution History from U.S. Appl. No. 11/414,786, dated Jul. 30, 2008 through Sep. 21, 2015, 236 pp.
Prosecution History from U.S. Pat. No. 7,623,919, dated Sep. 27, 2007 through Oct. 9, 2009, 62 pp.
Prosecution History from U.S. Pat. No. 8,355,783, dated Jun. 5, 2012 through Oct. 30, 2012, 24 pp.

* cited by examiner

EVENT-BASED LEAD IMPEDANCE MONITORING

This application claims the benefit of U.S. provisional application No. 60/676,250, filed Apr. 29, 2005, the entire content of which is incorporated herein by reference.

TECHNICAL FIELD

The invention relates to implantable medical devices and, more particularly, implantable medical devices that provide electrical sensing and/or stimulation.

BACKGROUND

Medical devices are used to treat patients suffering from a variety of ailments and symptoms. Often, medical devices treat such ailments and symptoms with electrical stimulation delivered to patient tissue via electrodes on one or more leads. For some conditions, the medical device also senses electrical activity within the patient via the electrodes. Based on the electrical activity, the medical device may detect a symptomatic event, and deliver stimulation to treat the event in response to the detection.

For example, many patients suffer from epilepsy, which is a condition that occurs when electrical signals in the brain are disrupted, e.g., hypersynchronized, causing a seizure. Occurring repeatedly, each seizure may cause a brief change in a patient's body movements, awareness, emotions, or senses. These seizures may affect a patient's ability to hold a job, drive a car, enjoy certain activities, or conduct other activities. Brain stimulation has been used to treat some epilepsy patients. For example, implantable medical devices have been used to electrically sense the beginning of a seizure and, if appropriate, deliver electrical stimulation to the brain to terminate the seizure. Applying stimulation in this manner may significantly increase a patient's quality of life.

A single lead may have a plurality of electrodes, and multiple conductors, each corresponding to one or more of the electrodes. The lead may be directly connected to a medical device, or may be connected to the medical device via one or more lead extensions. Conductors within a lead extension couple the conductors within a lead to the implantable medical device. An electrode, the conductors that couple the electrode to the implantable medical device, and tissue proximate to the electrode may be referred to as an electrical "path," through which the implantable medical device may sense electrical activity within a patient and/or deliver stimulation to the patient.

Over time, the impedance of such an electrical path may change due to, for example, degradation of the lead material or tissue growth proximate to the electrode. In some cases, the insulation of a lead may fail, causing a short between two electrical paths. In other cases, a conductor may fracture. Fractures may be caused by bending, twisting, compression, or tension stresses resulting from patient movement. Fractures occur with greatest frequency when implanted leads extend subcutaneously through the neck and to the cranium of a patient, such as might be the case for brain stimulation to treat epilepsy. Shorts and fractures may be intermittent. Shorts, fractures and other electrical path impedance changes may impair the ability of a medical device to effectively treat a patient.

SUMMARY

In general, the invention is directed to techniques for identifying dysfunctional electrical paths among the paths provided by one or more leads coupled to a medical device. More particularly, a medical device determines whether a symptomatic event within the patient, such as a seizure, is detected. Based on the determination, the medical device measures the impedance of one or more electrical paths associated with one or more leads coupled to the medical device.

Based on the measured impedances, the medical device may identify and respond to dysfunctional paths, e.g., paths that may be unable to provide adequate or reliable sensing or therapy due to, for example, degradation of the lead material, tissue growth proximate to an electrode, a short, or a fracture. If the medical device identifies a dysfunctional electrical path based on the measured impedance, the medical device may disable the dysfunctional electrical path. For example, the medical device may modify a stimulation or sensing program to not use the dysfunctional electrical path. Additionally or alternatively, the medical device may change other parameters of the program, such as sensing gain or stimulation amplitude, to compensate for the dysfunctional path. In this manner, the medical device may identify and inaccurate symptomatic event detection, avoid future inaccurate symptomatic event detection and, where the medical device delivers a therapy in response to such detection, such as stimulation via the electrical paths, avoid inappropriate therapy delivery.

Additionally or alternatively, the medical device, or a programmer or other external device in communication the medical device, may provide an alarm to the patient in response to the detection of one or more dysfunctional paths. The alarm may be audible, vibratory, tactile, stimulatory, visual, or the like. The alarm may cause the patient to visit a clinician regarding the lead malfunction, where the clinician may take one or more corrective actions, such as disabling dysfunctional paths, modifying programs or, if necessary, replacing leads. The medical device or programmer may store information regarding the dysfunctional path, which may be provided to the clinician, e.g., via the programmer, or another programmer or computing device at a clinic.

The medical device monitors electrical activity within a patient via electrical paths to detect the symptomatic event. A symptomatic event may be a seizure. However, the invention is not so limited, and the symptomatic event may alternatively be any neurological, gastrological, urological, muscular, or cardiac symptomatic event detectable via electrical paths associated with a lead.

The medical device may measure the impedances of the electrical paths in response to detecting symptomatic event. In some embodiments, the medical device also delivers stimulation via the electrical paths in response to the detection. For example, in response to detecting a seizure, the medical device may deliver electrical stimulation to terminate the seizure. The impedance measurements may be performed before, after, or during delivery of the stimulation.

As examples, the medical device may measure the impedance of the electrical paths in response to detecting a symptomatic event, failing to detect a symptomatic event for a period of time, or failing to detect a symptomatic event when other information, such as a signal from the patient, indicates that the symptomatic event occurred. As other examples, the medical device may measure the impedance of the electrical paths in response to detecting a symptomatic event with a duration greater than a threshold, such as a status seizure, or a plurality of symptomatic events that occur at a frequency greater than a threshold, e.g., based on an apparently high seizure burden. Such conditions may be unusual, and indicate the possibility that a dysfunctional electrical path is causing false symptomatic event detections.

In one embodiment, the invention is directed to a method that comprises monitoring electrical activity within a patient via a plurality of implanted electrodes, determining whether a symptomatic event is detected based on the electrical activity, and automatically measuring an impedance of at least one of a plurality of electrical paths, each of the electrical paths associated with at least one of the electrodes, based on the determination.

In another embodiment, the invention is directed to a medical device comprising impedance measurement circuitry configured to measure an impedance of each a plurality of electrical paths, and a processor. The processor monitors electrical activity within a patient via the plurality of implanted electrodes, each of the electrodes associated with one of the paths, determines whether a symptomatic event is detected based on the electrical activity, and automatically controls the impedance measurement circuitry to measure an impedance of at least one of the plurality of electrical paths based on the determination.

In an additional embodiment, the invention is directed to a system comprising means for monitoring electrical activity within a patient via a plurality of implanted electrodes, means for determining whether a symptomatic event is detected based on the electrical activity, and means for automatically measuring an impedance of at least one of at least one of a plurality of electrical paths, each of the electrical paths associated with at least one of the electrodes, based on the determination.

Further, in other embodiments, the invention is directed to a computer readable media comprising instructions. The instructions may cause a programmable processor to perform any of the methods described herein.

In various embodiments, the invention may provide one or more advantages. For example, measuring electrical path impedances in response to a determination as to whether a symptomatic event is detected, rather than according to a schedule, may reduce power consumption, e.g., improve battery life or lengthen recharge intervals, by eliminating unnecessarily frequent automatic measurements. Further, the impedances measured in response to such determinations may be more probative than automatic measurements. For example, measuring electrical path impedances in response to detection of a symptomatic event may allow an intermittent electrical path dysfunction that causes faulty symptomatic event detection to be identified. Such an intermittent path dysfunction may not have been present at the time of a scheduled path impedance measurement.

Further, by measuring electrical path impedances in response to a determination as to whether a symptomatic event is detected, dysfunctional electrical paths may be detected earlier then they would be by in clinic or scheduled impedance measurements. Earlier detection may allow the medical device, or other elements of a system including the device, to respond to the detection earlier, e.g., by taking one or more of the corrective or alerting actions discussed above. In addition to alerting a patient to visit a clinic to address the lead malfunction, as discussed above, an early alert in response to detection of a dysfunctional electrical path may cause a patient to take other action. For example, a patient may be able to avoid activities that may be compromised or more dangerous during impaired sensing or therapy. An epileptic patient may avoid driving in anticipation of undetected or untreated seizures, as an example. Further, a patient may begin an alternative therapy to the extent that an existing therapy is comprised by the dysfunctional path.

Additionally, identification of a dysfunctional lead based on impedance measurements performed in response to detecting or failing to detect a symptomatic event, may provide insight into the accuracy of previous symptomatic event detections and the efficacy of previously delivered therapy. Moreover, by disabling a dysfunctional electrical path, modifying or disabling sensing or stimulation programs that use a dysfunctional path, e.g., to "re-route" sensing or therapy to one or more other paths, or the like, the medical device may improve the effectiveness of future sensing and therapy.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
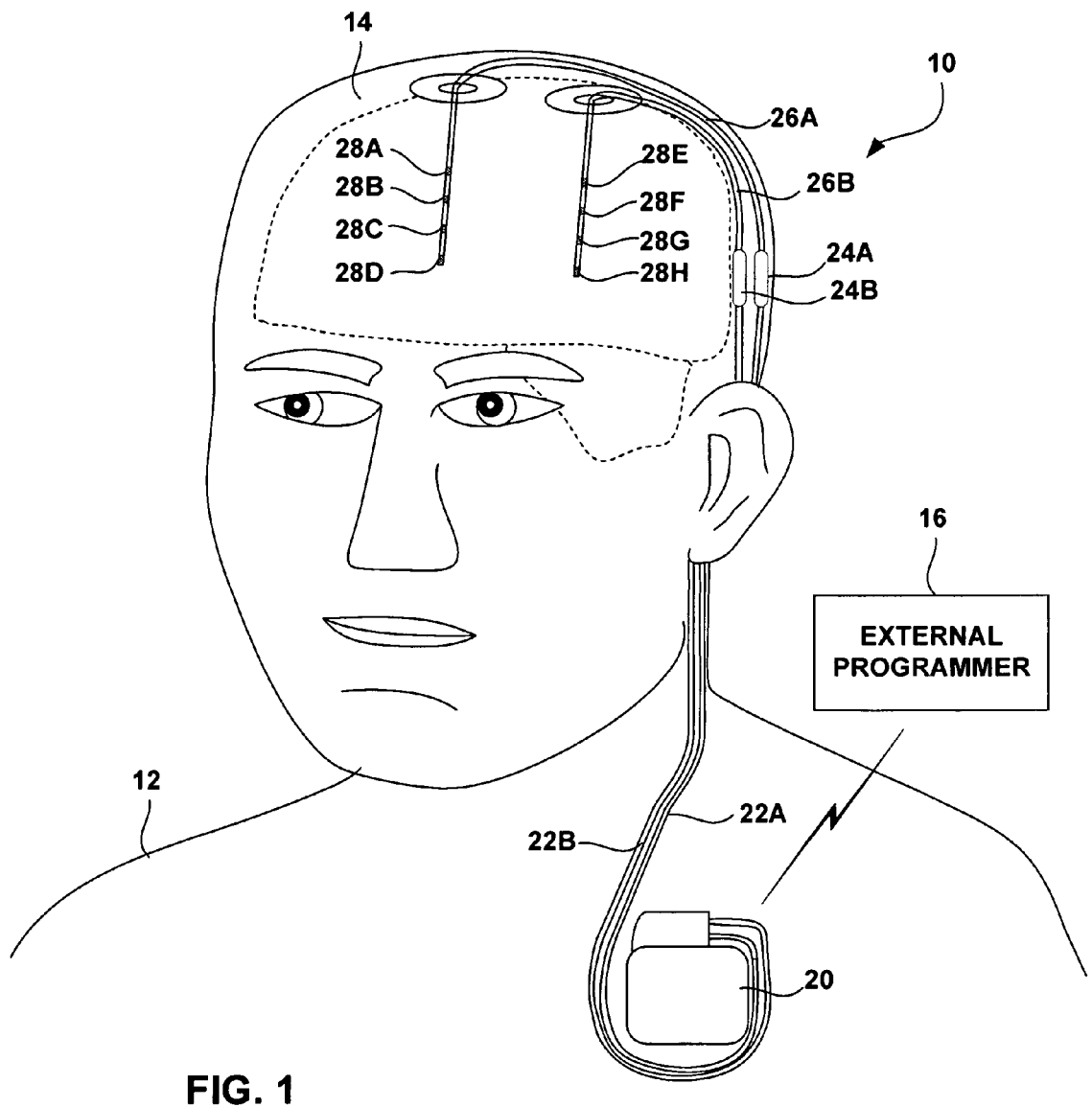
FIG. 1 is a conceptual diagram illustrating a system that includes a medical device that measures electrical path impedances based on a determination as to whether a symptomatic event has been detected.

FIG. 1 is a conceptual diagram illustrating a system 10 that includes an implantable medical device (IMD) 20 implanted within a patient 12. In the example illustrated by FIG. 1, IMD 20 is coupled to a leads 26A and 26B (collectively "leads 26") by respective lead extensions 22A and 22B (collectively "lead extensions 22"). Lead extensions 22 and leads 26 are coupled by respective connectors 24A and 24B (collectively "connectors 24"). Leads 26 include a plurality of electrodes 28A-28H (collectively "electrodes 28") at their distal ends, which are implanted within the brain 14 of patient 12.

The number and position of electrodes 28, leads 26, lead connectors 24 and extensions 22 illustrated in FIG. 1 are exemplary. For example, system 10 may include any one or more leads 26, each including one or more electrodes 28, and need not include any extensions 22 or connectors 24. Leads 26 may be a substantially cylindrical, percutaneously implantable leads, and electrodes 28 may be ring electrodes.

However, in other embodiments, leads 26 may have other shapes, such as paddle-like shapes with electrodes located on one or more sides of the paddle, or may include a complex, multi-dimensional electrode array geometry. For example, lead 26 may have a substantially cylindrical shape, and include a plurality of non-ring electrodes located at various circumferential and axial positions thereon. As another example, a distal end of one of leads 26 may include a "cuff-like" element, with one or more leads disposed about the interior of the cuff. Further, in addition to or as an alternative to electrodes 28 located on leads 26, one or more electrodes with associated electrical paths may be located on or near, or provided by, the housing or header of IMD 20.

IMD 20 senses electrical activity via electrodes 28. IMD 20 may detect a symptomatic event based on the electrical activity. For purposes of illustrating the invention, it will be assumed that patient 12 is prone to seizures, i.e., has epilepsy. IMD 20 detects electrical activity within brain 14 via a plurality of electrodes 28 to detect a seizure, which is an example of a "symptomatic event" that may be detected by a medical device according to the invention.

In some embodiments, IMD 20 delivers stimulation via electrodes 28. IMD 20 may deliver stimulation in response to detection of a symptomatic event, e.g., to provide a closed-loop therapy. For example, in response to detecting a seizure, IMD 20 may deliver electrical stimulation to target tissues, such as the hippocampus, anterior nucleus of the thalamus, temporal lobe, or other regions in brain 14, via a plurality of electrodes 28 to terminate the seizure.

As will be described in greater detail below, IMD 20 also measures the impedance of one or more "electrical paths" based on a determination as to whether a symptomatic event has been detected. An "electrical path" typically includes one of electrodes 28, the conductors and contacts within lead 26, connector 24 and extension 22 associated with the electrode, and tissue proximate to the electrode. Accordingly, because lead 26 includes four electrodes 28, the lead may include four electrical paths. In other embodiments, however, an electrical path may include a plurality of electrodes 28 coupled to IMD 20. In either case, IMD 20 senses electrical activity and delivers stimulation via a plurality of electrical paths, each path including one or more electrodes 28.

Based on the measured impedances, IMD 20 may identify one or more dysfunctional electrical paths. An electrical path may be "dysfunctional" due to material degradation, tissue growth proximate to the one of electrodes 28 associated with the electrical path, a short, or a fracture in one of the conductors within lead 26 or extension 22 that is associated with the electrical path. As will be described in greater detail below, IMD 20 may respond in a variety of ways to identification of a dysfunctional electrical path, including disabling the path. For example, IMD 20 may modify sensing or stimulation programs to not include the path, which may involve selecting one or more different electrodes or electrode combinations for the programs. As another example, IMD 20 may respond to identification of a dysfunctional electrical path by modifying other parameters of the programs, such as sensing gain or stimulation amplitude, to compensate for the dysfunctional path. Further, IMD 20 may notify patient 12 or a clinician of the detection of a dysfunctional electrical path.

The invention is not limited to implementation by IMDs that detect and treat seizures. A symptomatic event may be any neurological, gastrological, urological, muscular, or cardiac symptom detectable via electrodes. Furthermore, a symptomatic event may be any event that IMD actively seeks to sense as a symptom, e.g., for purposes of patient monitoring and/or in order to provide responsive therapy.

For example, an IMD may be coupled to electrodes implanted within or near the brain or spinal cord to detect symptomatic events such as increased or more frequent electrical signals indicative of increasing pain levels. As another example, an IMD may be coupled to electrodes implanted within or near the brain or spinal cord, or within muscle of a patient to detect symptomatic events such as increased or more frequent electrical signals indicative of tremor or other movement disorders.

Further, an IMD may be coupled to electrodes implanted near the spinal cord, a cranial or peripheral nerve such as the sacral nerve, the bladder, or colon to detect symptomatic events such as electrical signals associated with incontinence events, implanted near the stomach to detect gastric motility events, or implanted within or near the heart of a patient to detect symptomatic events such as a cardiac arrhythmia. Accordingly, the invention is not limited to neurostimulators, and is further not limited to medical devices that provide stimulation, or even to implanted medical devices. Any implantable or external medical device that senses electrical activity within a patient via one or more electrical paths may detect symptomatic events, and measure the impedance of the electrical paths, in the manner described herein.

As illustrated in FIG. 1, system 10 may also include an external programmer 16 that transcutaneously communicates with IMD 20, such as via radio-frequency telemetry. External programmer 16 may be a hand-held device associated with patient 12, or it may be embodied as a more fully-featured device typically associated with a clinician. IMD 20 may alert patient 12 if a dysfunctional electrical path has been identified itself, e.g., via a vibratory, auditory, stimulatory or other alert. Further, in some embodiments, IMD 20 may alert patient 12 via programmer 16, which may provide or other alarm to patient 12 in response to receiving a signal from IMD 20.

In some embodiments, IMD 20 may provide more detailed information regarding the detection of the dysfunctional path to programmer 16, which the programmer may then provide to patient 12 or a clinician, e.g., via a display. Programmer 16 may also suggest a course of action for the user based on such signals or information. For example, based on a signal from IMD 20, programmer 16 may advise patient 12 that sensing or therapy may have been impaired or modified, or direct the patient to visit a clinician. Similarly, based on more detailed information from IMD 20, programmer 16 may advise the clinician which path is dysfunctional, identify any actions automatically taken by IMD 20 in response to the identification of a dysfunctional electrical path, or advise the clinician to reconfigure or reprogram the IMD 20 to avoid use of the electrical path using any of the techniques discussed above. In some cases, programmer 16 may advise the clinician to replace one or more of leads 26, connectors 24 and extensions 22.

Figure 2:
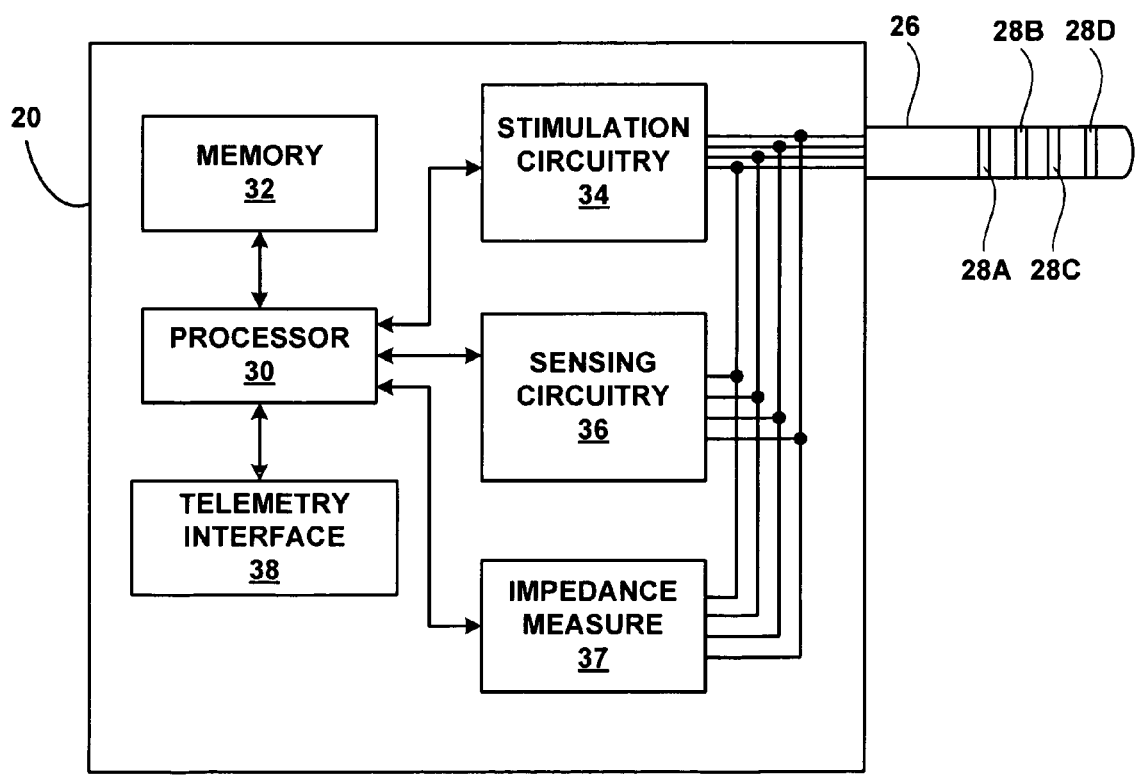
FIG. 2 is a functional block diagram further illustrating the medical device of FIG. 1.

FIG. 2 is a functional block diagram further illustrating IMD 20 according to one embodiment. In the illustrated example, IMD 20 includes a processor 30, memory 32, stimulation circuitry 34, sensing circuitry 36, impedance measurement circuitry 37, a telemetry interface 38, and a power source 40. In FIG. 2, electrical lead 26A is shown directly coupled to IMD 20, rather than via extension 22, for ease of illustration. Further, IMD 20 is shown coupled only to lead 26A in FIG. 2, rather than both of leads 26, for ease of illustration. Conductors in lead 26A are shown electrically coupled to stimulation circuitry 34, sensing circuitry 36, and impedance measurement circuitry 37.

Sensing circuitry 36 receives signals via lead 26A and electrodes 28 that represent electrical activity within patient 12 and, more particularly, brain 14. Sensing circuitry 36 may include amplifiers, filters, analog-to-digital converters, or other circuitry. Processor 30 monitors the signals to detect a symptomatic event.

As will be described in greater detail below, processor 30 determines whether a symptomatic event is detected, and controls impedance measurement circuitry 37 to measure the impedance of one or more of the electrical paths associated with electrodes 28 based on the determination. Impedance measurement circuitry 27 may include resistors, capacitors, or other known circuitry for sampling and/or holding a value of one or both of voltage or current when a signal is delivered by stimulation circuitry 34. Processor 30 may determine the impedance based on the measured voltage and/or current using any of a variety of known techniques.

For example, in some embodiments, stimulation circuitry 34 delivers a voltage pulse with a decay, and measurement circuitry 37 samples and holds the final voltage value of the pulse at the end of the pulse. Based on the initial, e.g., programmed, voltage for the pulse, and the sampled final voltage, processor 30 may determine the impedance associated with a combination of electrodes using known techniques, such as those described in commonly-assigned U.S. Pat. No. 6,978,171, which issued to Goetz et al. on Dec. 20, 2005, and is incorporated herein in its entirety by reference. Equations or the like used by processor 30 to determine the impedance or current may be stored in a memory 32.

Processor 30 may control stimulation circuitry 34 to deliver a dedicated, e.g., sub-threshold, signal, and control impedance measurement circuitry 37 to measure the impedance during the delivery. The dedicated signal may be, for example, a pulse having an amplitude or pulse width significantly lower than that of therapeutic stimulation pulses. Because of their low amplitude and/or pulse width, such dedicated pulses may not result in any therapeutic or adverse effects, e.g., may not be above a threshold sufficient to activate any nerves or other tissues, and therefore may be referred to as "sub-threshold" pulses.

In other embodiments, processor 30 controls impedance measurement circuitry 37 to measure the impedance during delivery of therapeutic stimulation to patient 12 by stimulation circuitry 34. Processor 30 may control delivery of stimulation in response to detection of a symptomatic event. As discussed above, the symptomatic event may be a seizure, and stimulation circuitry 34 may deliver stimulation to terminate the seizure.

Stimulation circuitry 34 may include one or more constant-voltage or constant-current output pulse generators, and switches or the like to couple the pulse generators to electrodes 28 as controlled by processor 30. However, the invention is not limited to embodiments in which stimulation circuitry 34 delivers pulses. In other embodiments, stimulation circuitry 34 may deliver signals with any of a variety of waveforms, such as sine or square waves.

Based on the measured impedance for an electrical path, processor 30 may determine whether the path is dysfunctional. For example, processor 30 may compare the measured impedance to one or more threshold values stored in memory 32, such as both a high and low threshold value, and determine whether the electrical path is faulty based on the comparison. Processor 30 may initiate a variety of responses to a determination that an electrical path is dysfunctional, including providing a signal or information to patient 12 or a clinician via telemetry interface 38 and external programmer 16 (FIG. 1), as described above. Processor 30 may store an indication of a dysfunctional electrical path within memory 32 based on the determination, and later provide a signal or information via programmer 16 when interrogated by the programmer via telemetry interface 38. Other responses that may be initiated by processor 30 are described in greater detail below.

Memory 32 may store one or more sensing programs that define which electrodes, i.e., electrical paths, are to be used to sense symptomatic events. A sensing program may specify which of the electrical paths is a reference path for sensing. Memory 32 may also store one or more stimulation programs that define which electrodes, i.e., electrical paths, are to be used for delivery of stimulation, the order and timing at which they are used to deliver stimulation, and other characteristics of the stimulation, such as pulse amplitudes, widths and rates. Processor 30 controls stimulation and sensing circuitry 34 and 36 based on these programs. These programs and other instructions stored by memory 32 may, when executed by processor 30, cause the processor and IMD 14 to perform any of the methods described herein.

Processor 30 may include any one or more of a microprocessor, a controller, a digital signal processor (DSP), an application specific integrated circuit (ASIC), a field-programmable gate array (FPGA), discrete logic circuitry, or the like. Memory 32 may include for example any volatile, non-volatile, magnetic, optical, or electrical media. For example, memory 32 may include any one or more of a random access memory (RAM), read-only memory (ROM), non-volatile RAM (NVRAM), electronically erasable programmable ROM (EEPROM), flash memory, or the like.

Figure 3:
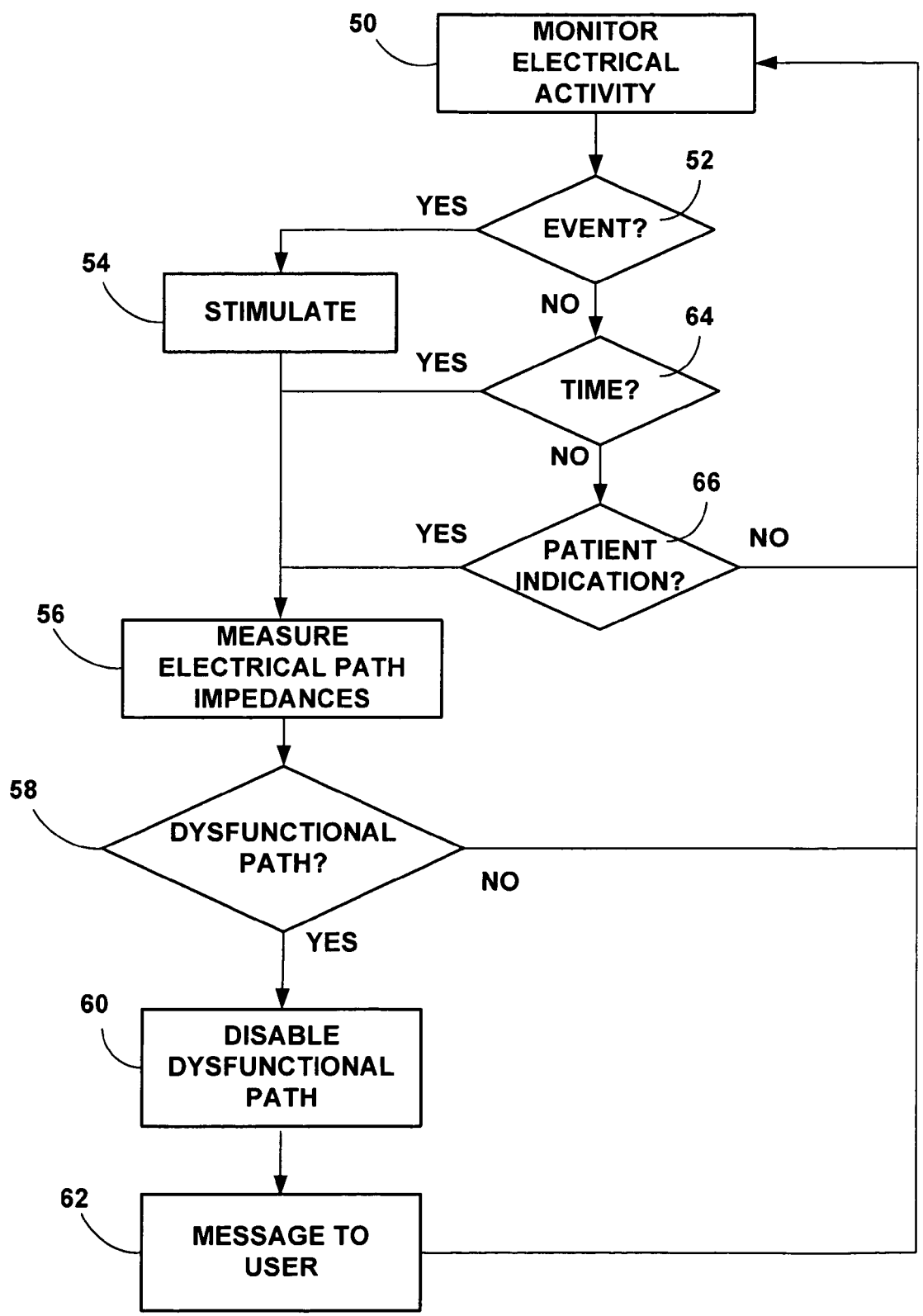
FIG. 3 is a flow diagram illustrating an example method for measuring electrical path impedances based on a determination as to whether a symptomatic event has been detected.

FIG. 3 is a flow diagram illustrating an example method for measuring electrical path impedances based on a determination as to whether a symptomatic event has been detected, which may be performed by IMD 20. According to the example method, IMD 20 and, more particularly, processor 30 of IMD 20, monitors electrical activity within patient via electrodes 28 (50). Based on the electrical activity, processor 30 determines whether a symptomatic event, such as a seizure, is detected (52). If a symptomatic event is detected, processor 30 controls stimulation circuitry 34 to deliver stimulation via electrodes 28 (54), e.g., to terminate the seizure.

Processor 30 also controls impedance measurement circuitry 37 to measure the impedance of at least one of the plurality of electrical paths associated with electrodes 28 in response to detection of symptomatic event (56). Processor 30 may determine impedances for electrical paths, e.g., electrodes, used to deliver the therapeutic stimulation, e.g., by controlling impedance measurement circuitry 37 to measure impedance during delivery of the stimulation. Additionally or alternatively, processor 30 may determine impedances for electrical paths not used to deliver stimulation.

For example, processor 30 may determine impedances for all electrical paths, or only those used to detect symptomatic events, or those that detected the particular symptomatic event that triggered stimulation. As discussed above, in addition or as an alternative to measurement during delivery of therapeutic stimulation, processor 30 may determine impedances for any desired electrical paths by controlling stimulation circuitry 34 to deliver dedicated, e.g., subthreshold, signals via the paths, and controlling impedance measurement circuitry 37 to measure impedances based on the signals. Although FIG. 3 illustrates impedance measurements as occurring after delivery of therapy, processor 30 may initiate such non-therapeutic measurements in response to detection of the symptomatic event at any time before or after delivery of therapeutic stimulation.

Processor 30 may control circuitry 37 to measure impedance after every detected symptomatic event, or after every $N^{th}$ detected event, where N is an integer greater than 1. Measuring more frequently may allow IMD 20 or other devices, such as programmer 16, to more accurately identify when an electrical path failed. In embodiments in which IMD 20 records data based on sensing or therapy delivery via the path, accurate identification of failure may indicate what data is not reliable. On the other hand, frequent measurements consume energy, e.g., deplete an IMD battery, and may result in too great an amount of measurement related data stored in memory 32.

Further, processor 30 may in some embodiments, conditionally control circuitry 37 to measure impedances in response to a symptomatic event based on its correlation or lack of correlation with some other event, such as input from the patient indicating occurrence of a symptomatic event, or an analysis if characteristics of the signal monitored via sensing circuitry 36, such as amplitude, frequency, or derivatives thereof. By only measuring impedances at such times, processor 30 may achieve the power consumption and memory benefits for IMD 10 discussed above. Further, correlative events, such as low signal quality may increase the likelihood that the detected "event" is, in fact, the result of a dysfunctional signal path.

Based on the measured impedances, processor 30 determines whether any of the electrical paths are dysfunctional (58). As indicated above, processor 30 may determine that an electrical path is dysfunctional by comparing the measured impedance to one or more threshold values stored in memory. In particular, if the impedance value is above or below an applicable threshold impedance value stored in memory 32, processor 30 may determine that the electrical path is dysfunctional.

If processor 30 identifies a dysfunctional path, processor 30 may disable that path (60). For example, processor 30 may select stimulation and sensing programs that do not use the dysfunctional path, or modify stimulation and sensing programs such that they do not use the dysfunctional path, or otherwise compensate for the dysfunctional path. Further, if the dysfunctional path acts as a reference path for sensing, processor 30 may select a new electrical path to act as the reference path. Processor 30 may also provide an alert or message to a user, such as patient 12 or a clinician, via programmer 16, as discussed above (62). If processor 30 does not identify a dysfunctional path (58), processor 30 continues to monitor electrical activity within the patient (50).

When processor 30 has not detected a symptomatic event (52), processor 30 may further determine whether a threshold time period has passed since the last detection of a symptomatic event (64). A long quiescent period may be indicative of one or more dysfunctional electrical paths. Further, processor 30 may determine whether an indication that a symptomatic event occurred has been received from patient 12 (66). Failure to detect a reported symptomatic event based on the monitored electrical activity may also be indicative of one or more dysfunctional electrical paths. Processor may receive the indication from patient, via programmer 16, by detecting "tapping" proximate to the implant site of IMD 10 via an accelerometer or piezoelectric element, by detecting placement of magnet proximate to IMD 10, or by detecting an independent physiological indication of the event via another sensor, such as detecting a falling event accompanying a seizure via an accelerometer or piezoelectric element. Processor 30 may control impedance measurements and identify dysfunctional paths (56-62) as described above, in response to identifying a time period without detection (64), or a failed detection (66). In some embodiments, processor 30 may require one or more such indicated failures prior to controlling an impedance measurement, e.g., to reduce energy and memory consumption, as described above.

Figure 4:
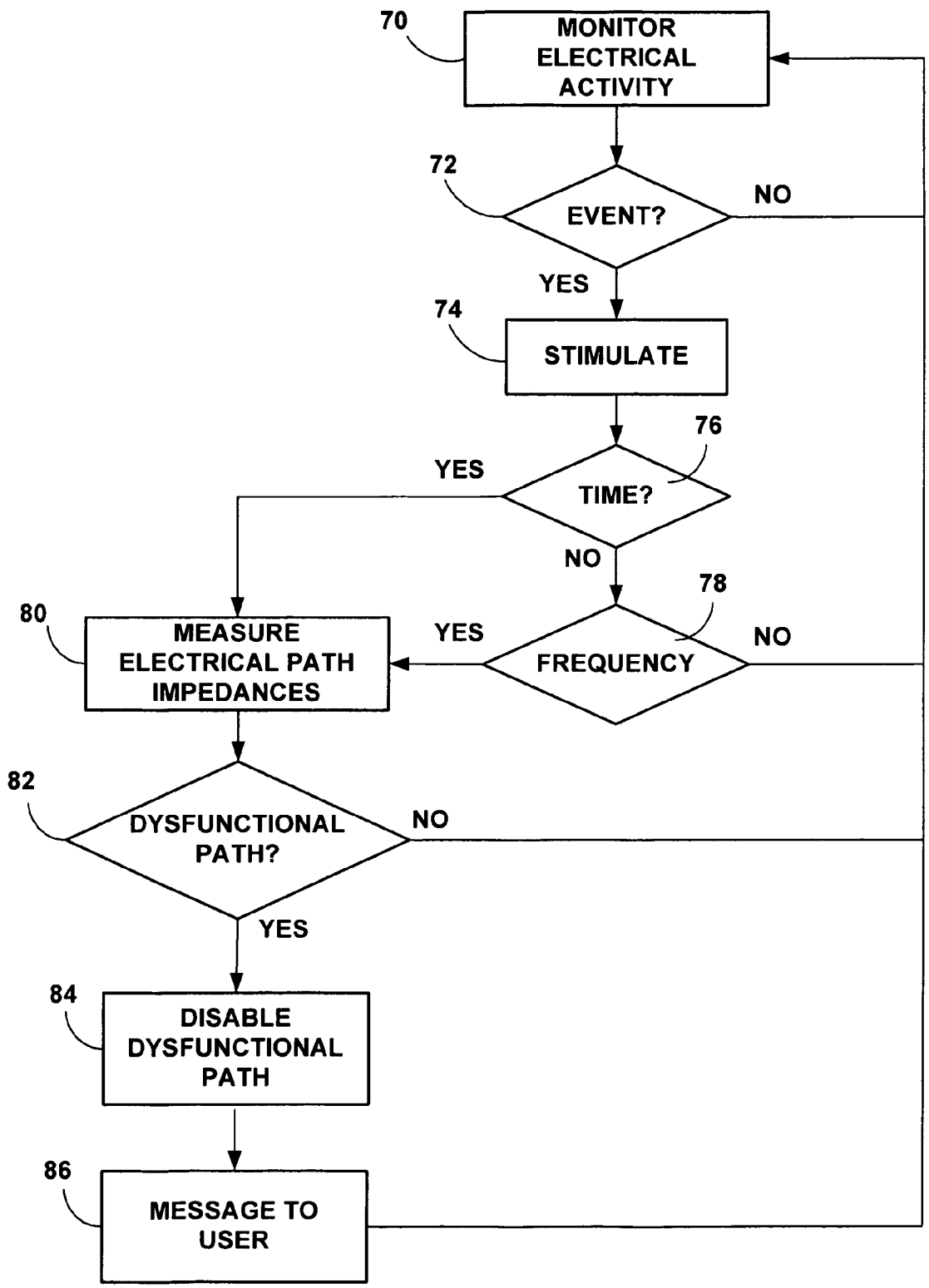
FIG. 4 is a flow diagram illustrating another example method for measuring electrical path impedances based on a determination as to whether a symptomatic event has been detected.

FIG. 4 is a flow diagram illustrating another example method for measuring electrical path impedances based on a determination as to whether a symptomatic event has been detected that may be performed by IMD 30. According to this example method, processor 30 monitors electrical activity (70), determines whether a symptomatic event is detected (72), and controls delivery of therapeutic stimulation in response to detection of a symptomatic event (74), as described above.

However, in this embodiment, processor 30 determines whether the symptomatic event has lasted longer than a threshold time (76), or whether the current symptomatic event and previously detected symptomatic events have occurred at greater than a threshold frequency (78). With respect to detection of seizures, a long seizure is known as a status event, which may generally be a rare but significant event for determining the severity of epilepsy and other important disorders such as Sudden Unexpected Death in Epilepsy Patients (SUDEP) for patient 12. However, detection of such an event may alternatively indicate a lead fracture. Similarly frequency of seizures is a factor in the determination of the severity of epilepsy. However, a high frequency of symptomatic event detections may alternatively indicate signal quality issues such as "railing," which may be caused by an intermittent lead fracture. "Railing" refers to repeated movement of a signal between a very low or zero value, and a significantly higher value, which may be misinterpreted as a seizure.

In response to detection of high-duration or high-frequency symptomatic events, processor 30 may measure impedances, identify dysfunctional paths, and respond to such identification (80-86) as described above. In this manner, processor 30 may better distinguish clinically significant symptomatic events from lead failures. Further, by identifying dysfunctional electrical paths and, for example, disabling such paths, processor 30 may avoid continued erroneous event detections and unnecessary delivery of therapy.

Many embodiments of the invention have been described. However, one of ordinary skill in the art will appreciate that various modifications may be made to the described embodiments without departing from the scope of the invention. For example, although primarily described herein with reference to embodiments in which an IMD both senses electrical activity of patient and delivers stimulation therapy to the patient via electrodes and electrical paths, the invention is not so limited. In other embodiments, an IMD may additionally or alternatively deliver other, non-stimulation therapies, such as delivery of one or more drugs or other therapeutic agents. For example, IMD may additionally or alternatively deliver one or more gabapentin or baclofen to, or control a peltier device to heat or cool, the brain or other tissues of a patient.

Additionally, functions described herein as performed by IMD 20 may instead be performed by programmer 16, other computing devices, other implanted or external medical devices, or any combination thereof, with or without the IMD. In some cases, programming or other computing devices may communicate with an IMD via a network to cooperatively perform the techniques described herein. For example, the alarms or other information provided to the patient or clinician directly by the IMD (audible alarm, vibration, perceptible stimulation, etc., or by cooperation of IMD with an external device (e.g. programmer, telemedicine device, patient device, second implantable or wearable medical device, etc.).

Other devices, such as programmer 16, may receive symptomatic event detection information from IMD 20, control IMD 20 to measure impedance, receive impedance measurements from IMD 20, and respond in any way described herein with reference to IMD 20. Such devices may include any of the types of processors and memory described above with respect to processor 30 and memory 32 of IMD 14. Further, while the IMD and programmer may contain fixed memory, the external programmer or other device may additionally contain a removable memory or network connectivity capability to enable easy data transfer for offline data analysis. The memory of programmer 16 may store program instructions for execution by a processor, that cause the processor to perform the methods described herein. These and other embodiments are within the scope of the following claims.

The invention claimed is:

1. A method comprising:
monitoring, by a processor, electrical activity within a patient via a plurality of implantable electrodes;
detecting, by the processor, a neurological event based on the electrical activity; and
automatically measuring, with impedance measurement circuitry, an impedance of at least one of a plurality of electrical paths in response to the detection, each of the electrical paths associated with a respective one or more of the plurality of implantable electrodes.

2. The method of claim 1, wherein detecting the neurological event comprises detecting a seizure.

3. The method of claim 1, wherein detecting the neurological event comprises:
determining a duration of the neurological event; and
comparing the duration to a threshold value,
wherein measuring the impedance comprises measuring the impedance based on the comparison.

4. The method of claim 1, wherein detecting the neurological event comprises:
detecting a plurality of neurological events;
determining a frequency of the neurological events; and
comparing the frequency to a threshold value,
wherein measuring the impedance comprises measuring the impedance based on the comparison.

5. The method of claim 1, wherein detecting the neurological event comprises detecting the neurological event via a subset of the electrodes, and measuring the impedance comprises measuring the impedance in response to detecting the neurological event via the subset of electrodes.

6. The method of claim 1, further comprising identifying a dysfunctional electrical path based on the measured impedance.

7. The method of claim 6, further comprising disabling the dysfunctional electrical path.

8. The method of claim 6, further comprising modifying at least one of a stimulation program or a sensing program to not use the dysfunctional electrical path,
wherein the stimulation program defines which of the plurality of electrical paths are to be used for the delivery of stimulating to the patient, and
wherein the sensing program defines which of the plurality of electrical paths are to be used to sense the monitored electrical activity within the patient.

9. The method of claim 6, wherein the dysfunctional electrical path comprises a reference electrical path for sensing, the method further comprising selecting another of the plurality of electrical paths as the reference electrical path.

10. The method of claim 1,
wherein detecting the neurological event based on the electrical activity comprises detecting a plurality of neurological events based on the electrical activity, and
wherein measuring the impedance comprises measuring the impedance in response to detection of every $N^{th}$ neurological event of the plurality of neurological events, and N is an integer greater than 1.

11. The method of claim 1, further comprising evaluating at least one characteristic of a signal that includes the electrical activity, wherein measuring the impedance comprises measuring the impedance based on detecting the neurological event and the evaluation.

12. The method of claim 1, wherein monitoring electrical activity within the patient comprises monitoring electrical activity within a brain of the patient, and wherein detecting the neurological event based on the electrical activity comprises detecting the neurological event based on the monitored electrical activity within the brain.

13. A medical device comprising:
impedance measurement circuitry configured to measure an impedance of each of a plurality of electrical paths; and
a processor configured to monitor electrical activity within a patient via a plurality of implantable electrodes, each of the electrodes associated with one or more of the electrical paths, wherein the processor is further configured to detect a neurological event based on the electrical activity, and automatically control the impedance measurement circuitry to measure an impedance of at least one of the plurality of electrical paths in response to the detection.

14. The medical device of claim 13, wherein the neurological event comprises a seizure.

15. The medical device of claim 13, wherein the processor is further configured to determine a duration of the neurological event, compare the duration to a threshold value, and control the impedance measurement circuitry to measure the impedance based on the comparison.

16. The medical device of claim 13, wherein the processor is further configured to detect a plurality of neurological events, determine a frequency of the neurological events, compare the frequency to a threshold value, and control the impedance measurement circuitry to measure the impedance based on the comparison.

17. The medical device of claim 13, wherein the processor is further configured to detect the neurological event via a subset of the plurality of electrodes, and control the impedance measurement circuitry to measure the impedance in response to detecting the neurological event via the subset of the plurality of electrodes.

18. The medical device of claim 13, wherein the processor is further configured to identify a dysfunctional electrical path based on the measured impedance.

19. The medical device of claim 18, wherein the processor is further configured to disable the dysfunctional electrical path.

20. The medical device of claim 18, wherein the processor is further configured to modify at least one of a stimulation program or a sensing program to not include the dysfunctional electrical path,
wherein the stimulation program defines which of the plurality of electrical paths are to be used for the delivery of stimulating to the patient, and
wherein the sensing program defines which of the plurality of electrical paths are to be used to sense the monitored electrical activity within the patient.

21. The medical device of claim 18, wherein the dysfunctional electrical path is a reference electrical path for sensing the electrical activity within the patient, and the processor is further configured to select another of the plurality of electrical paths to be the reference electrical path.

22. The medical device of claim 13, wherein the processor is further configured to detect a plurality of neurological events based on the monitored electrical activity, and to control the impedance measurement circuitry to measure the impedance in response to detection of every $N^{th}$ neurological event of the plurality of neurological events, and N is an integer greater than 1.

23. The medical device of claim 13, wherein the processor is further configured to evaluate at least one characteristic of a signal that includes the electrical activity, and measure the impedance based on detecting the neurological event and the evaluation.

24. The medical device of claim 13, wherein the medical device comprises an implantable medical device.

25. The medical device of claim 24, wherein the implantable medical device comprises an implantable neurostimulator.

26. The medical device of claim 13, wherein the processor is configured to monitor electrical activity within a brain of the patient, and detect the neurological event based on monitored electrical activity within the brain.

27. A system comprising:
means for monitoring electrical activity within a patient;
means for detecting a neurological event based on the electrical activity; and
means for automatically measuring an impedance of at least one of a plurality of electrical paths in response to the detection of a neurological event, wherein each of the electrical paths is associated with at least one of a plurality of implantable electrodes coupled to the means for monitoring the electrical activity.

28. The system of claim 27, wherein the means for detecting the neurological event comprises means for detecting a seizure.

29. A method comprising:
monitoring, by a processor, electrical activity within a patient via a plurality of implantable electrodes;
determining, by the processor, that a neurological event has not been detected based on the electrical activity; and
automatically measuring, with impedance measurement circuitry, an impedance of at least one of a plurality of electrical paths in response to the determination, each of the electrical paths associated with at least one of the plurality of implantable electrodes.

30. The method of claim 29, wherein determining that the neurological event has not been detected comprises determining that the neurological event has not been detected for a threshold period of time, and measuring the impedance comprises measuring the impedance in response to the determination that the neurological event has not been detected for the threshold period of time.

31. The method of claim 29, wherein determining that the neurological event has not been detected comprises:
receiving an indication from the patient that the neurological event occurred; and
in response to receiving the indication, determining that the neurological event was not detected based on the electrical activity.

32. A medical device comprising:
impedance measurement circuitry configured to measure an impedance of each a plurality of electrical paths; and
a processor configured to monitor electrical activity within a patient via a plurality of implantable electrodes, each of the electrodes associated with one or more of the electrical paths, determine that a neurological event was not detected based on the electrical activity, and automatically control the impedance measurement circuitry to measure an impedance of at least one of the plurality of electrical paths in response to the determination.

33. The medical device of claim 32, wherein the processor is further configured to determine that the neurological event has not been detected for a threshold period of time, and to control the impedance measurement circuitry to measure the impedance in response to the determination that the neurological event has not been detected for the threshold period of time.

34. The medical device of claim 32, wherein the processor is configured to receive an indication from the patient that the neurological event occurred, and in response to the indication, determine that the neurological event was not detected based on the electrical activity.

* * * * *